(12) United States Patent
Hines et al.

(10) Patent No.: US 8,318,222 B2
(45) Date of Patent: Nov. 27, 2012

(54) TOPICAL SKIN CARE FORMULATION

(75) Inventors: Michelle Hines, Hickory Creek, TX (US); Greg Norman, Bedford, TX (US)

(73) Assignee: Mary Kay, Inc., Dallas, TX (US)

( * ) Notice: Subject to any disclaimer, the term of this patent is extended or adjusted under 35 U.S.C. 154(b) by 134 days.

(21) Appl. No.: 13/023,289

(22) Filed: Feb. 8, 2011

(65) Prior Publication Data

US 2011/0206793 A1  Aug. 25, 2011

Related U.S. Application Data

(60) Provisional application No. 61/306,327, filed on Feb. 19, 2010.

(51) Int. Cl.
*A61K 8/00* (2006.01)
*A61K 9/00* (2006.01)
*A61K 8/97* (2006.01)
*A61K 33/32* (2006.01)
*A61K 33/04* (2006.01)
*A61K 36/00* (2006.01)

(52) U.S. Cl. ............ 424/777; 424/47; 424/58; 424/642; 424/713; 424/714; 424/725

(58) Field of Classification Search .................. None
See application file for complete search history.

(56) References Cited

U.S. PATENT DOCUMENTS

| | | | |
|---|---|---|---|
| 4,386,067 A | 5/1983 | Guillon | 424/522 |
| 5,833,998 A | 11/1998 | Biedermann et al. | 424/401 |
| 5,939,082 A | 8/1999 | Oblong et al. | 424/401 |
| 6,217,888 B1 | 4/2001 | Oblong et al. | 424/401 |
| 6,429,218 B1 | 8/2002 | Scivoletto et al. | 514/356 |
| 6,455,055 B1 | 9/2002 | Walling et al. | 424/401 |
| 6,492,326 B1 | 12/2002 | Robinson et al. | 512/18.6 |
| 6,528,071 B2 | 3/2003 | Vatter et al. | 424/401 |
| 6,630,163 B1 * | 10/2003 | Murad | 424/464 |
| 2005/0004274 A1 * | 1/2005 | Healy et al. | 524/80 |
| 2007/0072785 A1 * | 3/2007 | Sahin Topkara et al. | 510/296 |
| 2007/0166253 A1 | 7/2007 | Kostick et al. | 424/63 |
| 2009/0117211 A1 * | 5/2009 | Schneider et al. | 424/747 |
| 2009/0136595 A1 | 5/2009 | Shah et al. | 424/649 |

FOREIGN PATENT DOCUMENTS

| | | |
|---|---|---|
| WO | WO 2009/068351 | 6/2009 |
| WO | WO 2009/109946 | 9/2009 |
| WO | WO 2009/138801 | 11/2009 |

OTHER PUBLICATIONS

"Butyrosperum Parkii (Shea Butter) Extract" *International Cosmetic Ingredient Dictionary and Handbook*, 12th Edition, vol. 1, Tara E. Gottschalck and John E. Baily, Eds., Washington, D.C.: The Cosmetic, Toiletry, and Fragrance Association, pp. 365-366, 2008.

"Niacinamide" *International Cosmetic Ingredient Dictionary and Handbook*, 12th Edition, vol. 2, Tara E. Gottschalck and John E. Baily, Eds., Washington, D.C.: The Cosmetic, Toiletry, and Fragrance Association, p. 1651, 2008.

* cited by examiner

*Primary Examiner* — Patricia Leith
*Assistant Examiner* — Catheryne Chen
(74) *Attorney, Agent, or Firm* — Fulbright & Jaworski L.L.P.

(57) ABSTRACT

Disclosed is a multi-beneficial topical skin care composition, and methods for its use, that can hydrate skin, increase the firmness of skin, reduce the appearance of fine lines or wrinkles on skin, and reduce the appearance of age spots on skin. The composition can include a combination of skin active ingredients comprising *euterpe oleracea* fruit extract, *punica granatum* sterols, caprooyl tetrapeptide-3, tocopherol or tocopherol acetate, and niacinamide, a combination of skin moisturizing agents comprising glycerin and *butyrospermum parkii*, a photo stable combination of sunscreen agents providing the composition with a sun protection factor (SPF) of at least about 15, and a dermatologically acceptable vehicle which imparts a non-greasy feel when applied to skin.

4 Claims, No Drawings

TOPICAL SKIN CARE FORMULATION

CROSS REFERENCE TO RELATED APPLICATIONS

The application claims the benefit of U.S. Provisional Application No. 61/306,327, filed Feb. 19, 2010. The contents of the referenced application(s) is incorporated by reference.

BACKGROUND OF THE INVENTION

A. Field of the Invention

The present invention relates generally to topical skin care compositions.

B. Description of Related Art

Ageing, chronic exposure to adverse environmental factors, malnutrition, fatigue, etc., can change the visual appearance, physical properties, or physiological functions of skin in ways that are considered visually undesirable. Examples of such changes include reduced skin elasticity, reduced skin firmness, increased sagging of the skin, development of lines and wrinkles, development of pits or nodules in skin, development of age spots, dry skin, etc. Current products on the market either do not provide a sufficient treatment option or require a multitude of different compositions to treat these physiological changes to skin.

SUMMARY OF THE INVENTION

The present invention provides an effective solution to skin exhibiting reduced elasticity, reduced firmness, increased sagginess, dryness, flakiness, fine lines and wrinkles, pits or nodules, damage caused by ultraviolet radiation, age spots, uneven skin, etc. In one aspect of the present invention, the solution is topical application of a composition to skin in need of treatment. The skin can be in the décolleté region (e.g., neck, shoulders, and/or upper chest), facial skin, and/or body skin (e.g., arms, hands, chest, abdomen, upper and lower back, legs, buttocks, feet, etc.) of a human. In particular embodiments, the skin can be in the décolleté region and/or hands. The composition can include a combination of skin active ingredients, wherein the skin active ingredients include *euterpe oleracea* fruit extract, *punica granatum* sterols, caprooyl tetrapeptide-3, tocopherol or tocopherol acetate, or niacinamide, or any combination thereof, or all of these ingredients. The composition can also include a combination of skin moisturizing agents, wherein the moisturizing agents include glycerin or *butyrospermum parkii* or both. The composition can also include a photo stable combination of sunscreen agents providing the composition with a sun protection factor (SPF) of at least about 15. Photo-stable refers to the ability of the composition to maintain an SPF of at least about 15 for a sufficient period of time after exposure to UV rays such as from the sun. In particular embodiments, the sunscreen agents include 2-ethylhexyl 2-hydroxybenzoate, 2-hydroxy-4-methoxyphenyl)-phenylmethanone, 2-ethylhexyl 2-cyano-3,3-diphenyl-2-propenoate, or 1-(4-methoxyphenyl)-3-(4-tert-butylphenyl)propane-1,3-dione, or any combination thereof, or all of these ingredients. The composition can also include a dermatologically acceptable vehicle which imparts a non-greasy feel when applied to skin. In particular embodiments, the composition includes at least 50%, 55%, 60%, 65%, 70%, 75%, 80%, 85%, 90%, or more w/w of water. In certain aspects, the composition can include 1 to 3% w/w of the total combination of skin active ingredients, 5 to 15% w/w of the total combination of skin moisturizing agents, and 10 to 15% w/w of the total combination of sunscreen agents. In other aspects, the composition can include 0.5, 1, 2, 3, 4, 5, 6, 7, 8, 9, 10%, or more of the total combination of skin active ingredients, 1, 2, 3, 4, 5, 6, 7, 8, 9, 10, 11, 12, 13, 14, 15, 16, 17, 18, 19, 20%, or more of the total combination of skin moisturizing agents, and 1, 2, 3, 4, 5, 6, 7, 8, 9, 10, 11, 12, 13, 14, 15, 16, 17, 18, 19, 20%, or more of the total combination of sunscreen agents. In certain embodiments, the topical skin care composition can include 0.001 to 0.02% w/w of *euterpe oleracea*, 0.1 to 1% w/w of *punica granatum* sterols, 0.00001 to 0.001% w/w of caprooyl tetrapeptide-3, 0.1 to 1% w/w of tocopherol or tocopherol acetate, 0.1 to 2% w/w of niacinamide, 3 to 7% w/w of glycerin, 1 to 3% w/w of *butyrospermum parkii*, and 10 to 15% w/w of the total combination of sunscreen agents. In one embodiment, composition can include 3 to 7% w/w of 2-ethylhexyl 2-hydroxybenzoate, 2 to 4% w/w of 2-hydroxy-4-methoxyphenyl)-phenylmethanone, 1 to 3% w/w of 2-ethylhexyl 2-cyano-3,3-diphenyl-2-propenoate, and 1 to 3% w/w of 1-(4-methoxyphenyl)-3-(4-tert-butylphenyl)propane-1,3-dione. The composition can be fragrance-free in that it does not have a discernable odor. The composition can include a combination of odor-neutralizing ingredients, which can help produce a fragrance-free composition. In particular aspects, the combination of odor neutralizing ingredients includes at least 1, 2, 3, 4, 5, or all 6 of the following: ethylene brassylate, isobutyl methyl tetrahydropyranol; methyl linalool; methylenedioxyphenyl methylpropanal; phenylisohexanol; and cyclamen aldehyde. In certain aspects, the dermatologically acceptable vehicle can include any one of, any combination of, or all of the following ingredients: (i) distearyldimonium chloride; (ii) butylene glycol; (iii) C12-15 alkyl benzoate; (iv) cetyl alcohol; (v) dimethicone; (vi) steareth-21; (vii) dipropylene glycol dibenzoate; (viii) phenoxyethanol; and (ix) silica. In certain aspects, the composition can include any one of, any combination of, or all of the following ingredients in the following amounts: (i) 2 to 5% w/w of distearyldimonium chloride; (ii) 2 to 5% w/w of butylene glycol; (iii) 1 to 3% w/w of C12-15 alkyl benzoate; (iv) 1 to 3% w/w of cetyl alcohol; (v) 0.1 to 2% w/w of dimethicone; (vi) 0.1 to 2% w/w of steareth-21; (vii) 0.1 to 2% w/w of dipropylene glycol dibenzoate; (viii) 0.1 to 2% w/w of phenoxyethanol; and (ix) 0.1 to 2% w/w of silica. The dermatologically acceptable vehicle can further include any one of, any combination of, or all of the following additional ingredients: (x) PPG-15 stearyl ether benzoate; (xi) hydrogenated lecithin; (xii) disodium EDTA; (xiii) sodium chloride; (ivx) triethanolamine; and (xv) a preservative. The composition can include any one of, any combination of, or all of the following additional ingredients: (x) 0.01 to 0.2% w/w of PPG-15 stearyl ether benzoate; (xi) 0.01 to 0.2% w/w of hydrogenated lecithin; (xii) 0.01 to 0.2% w/w disodium EDTA; (xiii) 0.01 to 0.2% w/w sodium chloride; and (ivx) 0.01 to 0.2% w/w triethanolamine. In certain aspects, the composition has a viscosity ranging from 20,000 cps to 500,00 cps, as measured on a Brookfield Viscometer using a TC spindle at 2.5 rpm at 25° C. (or any range or integer therein—e.g., 30,000, 40,000, 50,000, 60,000, 70,000, 80,000, 90,000, 100,000, 110,000, 120,000, 130,000, 140,000, 150,000, 160,000, 170,000, 180,000, 190,000, 200,000, 250,000, 300,000, 400,000, 450,000, 475,000, etc.). In certain aspects, the composition is formulated a cream. The cream can be an oil-in-water emulsion. The composition can be a multi-functional composition capable of hydrating skin, increasing the firmness of skin, reducing the appearance of fine lines or wrinkles on skin, and reducing the appearance of age spots on skin. In certain aspects, any one of, any combination of, or all of the skin active ingredients, moisturization agents, sunscreen agents, ingredients in the dermatologically acceptable vehicle, or any additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin. Such encapsulated ingredients can be incorporated into the compositions described throughout this specification.

The plant extracts (e.g., *euterpe oleracea, punica granatum*, etc.) identified throughout this specification can be obtained from any part of the plant. Non-limiting examples include extracts obtain from the whole plant, leaves, stems, flowers, flower buds, bark, roots, fruit, seeds, and any mixture of such parts. By way of example, the extract can be obtained from the whole fruit (e.g., fruit pulp and seeds), the whole plant (e.g., the entire plant is used to produce the extract), a particular part of the plant at the exclusion of another part (e.g., seed extract isolated from other parts of the plant), etc. The extract can be water-based, alcohol-based, oil-based, gel-based etc.

In particular aspects, the compositions can be formulated as emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (e.g., aqueous or hydro-alcoholic solutions), anhydrous bases (e.g., lipstick or a powder), gels, ointments, milks, pastes, aerosols, solid forms, eye jellies, etc. The compositions can also be formulated for topical skin application at least 1, 2, 3, 4, 5, 6, 7, or more times a day during use. In other aspects of the present invention, compositions can be storage stable or color stable, or both. It is also contemplated that the viscosity of the composition can be selected to achieve a desired result, e.g., depending on the type of composition desired, the viscosity of such composition can be from about 1 cps to well over 1 million cps or any range or integer derivable therein (e.g., 2 cps, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, 100000, 200000, 300000, 400000, 500000, 600000, 700000, 800000, 900000, 1000000 cps, etc., as measured on a Brookfield Viscometer using a TC spindle at 2.5 rpm at 25° C.).

The compositions of the present invention can also be modified to have a desired oxygen radical absorbance capacity (ORAC) value. In certain non-limiting aspects, the compositions of the present invention or the plant extracts identified throughout this specification can be modified to have an ORAC value per mg of at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 55, 60, 70, 80, 90, 95, 100, 200, 300, 400, 500, 600, 700, 800, 900, 1000, 2000, 3000, 4000, 5000, 6000, 7000, 8000, 9000, 10000, 15000, 20000, 30000, 50000, 100000 or more or any range derivable therein.

The compositions in non-limiting aspects can have a pH of about 6 to about 9. In other aspects, the pH can be 1, 2, 3, 4, 5, 6, 7, 8, 9, 10, 11, 12, 13, or 14.

Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, or more, or any integer or derivative therein. The compositions can be sunscreen lotions, sprays, or creams.

Also disclosed is a method of hydrating, increasing the firmness, reducing the appearance of fine lines or wrinkles, and/or reducing the appearance of age spots on skin comprising topically applying to the skin in need thereof any one of the topical skin compositions disclosed in this specification. The skin can be in the décolleté region (e.g., neck, shoulders, and/or upper chest), facial skin, and/or body skin (e.g., arms, hands, chest, abdomen, upper and lower back, legs, buttocks, feet, etc.). In particular embodiments, the skin can be in the décolleté region and/or hands. In certain embodiments, the composition is applied to dry skin, saggy skin, a fine line or wrinkle, and/or an age spot (e.g., liver spots, discolored spots, a freckles, sun spot, hyper-pigmented skin, etc.). The method is capable of hydrating, increasing the firmness, reducing the appearance of fine lines or wrinkles, and reducing the appearance of age spots on hand or neck skin with a single composition.

The compositions of the present invention can also increase the integrity of the dermal-epidermal junction ("DEJ"). This method can stimulate the production of proteins and enzymes in dermal and epidermal cells that aid in connecting the denial layer to the epidermal layer.

In another embodiment there is disclosed a method of stimulating dermal or epidermal cellular activity in sagging skin, skin that has reduced elasticity or reduced firmness, skin having fine lines and wrinkles, or skin pits or nodules comprising topically applying to the skin any one of the compositions disclosed throughout this specification.

Also disclosed is a method of reducing free-radical damage in skin or reducing oxidation of skin cells while also moisturizing skin. The method can include applying any one of the compositions of the present invention to skin in need of such treatment.

In other aspects, any one of the compositions disclosed throughout this specification can be used to treat or prevent a wide variety of skin conditions (in addition to those previously mentioned). Non-limiting examples of skin conditions include pruritus, spider veins, lentigo, age spots, senile purpura, keratosis, melasma, blotches, fine lines or wrinkles, nodules, sun damaged skin, dermatitis (including, but not limited to seborrheic dermatitis, nummular dermatitis, contact dermatitis, atopic dermatitis, exfoliative dermatitis, perioral dermatitis, and stasis dermatitis), psoriasis, folliculitis, rosacea, acne, impetigo, erysipelas, erythrasma, eczema, sun burns, burned skin, open wounds, skin-inflammatory skin conditions, etc. In certain non-limiting aspects, the skin condition can be caused by exposure to UV light, age, irradiation, chronic sun exposure, environmental pollutants, air pollution, wind, cold, heat, chemicals, disease pathologies, smoking, or lack of nutrition. As noted above, the skin can be in the décolleté region (e.g., neck, shoulders, upper chest), facial skin, and/or body skin (e.g., arms, chest, abdomen, upper and lower back, legs, buttocks, feet, etc.). The method can further comprise identifying a person in need of skin treatment. The person can be a male or female. The age of the person can be at least 1, 2, 3, 4, 5, 6, 7, 8, 9, 10, 15, 20, 25, 30, 35, 40, 45, 50, 55, 60, 65, 70, 75, 80, 85, 90, 95, or more years old, or any range derivable therein. The method can also include topically applying an amount effective to: increase the stratum corneum turnover rate of the skin; increase collagen synthesis in fibroblasts; increase cellular anti-oxidant defense mechanisms (e.g., exogenous additions of anti-oxidants can bolster, replenish, or prevent the loss of cellular antioxidants such as catalase and glutathione in skin cells (e.g., keratinocytes, melanocytes, langerhans cells, etc.) which will reduce or prevent oxidative damage to the skin, cellular, proteins, and lipids); inhibit melanin production in melanocytes; reduce or prevent oxidative damage to skin (including reducing the amount lipid peroxides and/or protein oxidation in the skin).

In certain embodiments, compositions of the present invention can decrease the amount of internal oxidation and/or external oxidative damage in a cell. In other aspects, the compositions can increase collagen synthesis in a cell. The compositions can also reduce skin inflammation, such as by reducing inflammatory cytokine production in a cell. Non-limiting examples of such cells include human epidermal keratinocyte, human fibroblast dermal cell, human melanocytes, three dimensional human cell-derived in vitro tissue equivalents comprising human keratinocytes, human fibroblasts, or human melanocytes, or any combination thereof (e.g., combination of human keratinocytes and human fibroblasts or a combination of human keratinocytes and human melanocytes).

Also disclosed is a method of lightening skin or evening skin tone comprising applying the compositions of the present invention to the skin. The method can further comprise identify a person in need of lightening skin or evening skin tone. The methods can further include inhibiting melanogenesis in a skin cell, inhibiting tyrosinase or tyrosinase synthesis in a skin cell, or inhibiting melanin transport to keratinocytes in a skin cell. The composition can act as an alpha melanin stimulatory hormone antagonist. The composition can even out pigmentation of the skin. In non-limiting aspect, lightening skin can include reducing the appearance of an age spot, a skin discoloration, a freckle, a sun spot, hyper-pigmented skin, etc., by topical application of the composition to the age spot, a skin discoloration, a freckle, a sun spot, hyper-pigmented skin, etc.

It is also contemplated that the compositions of the present invention can be included into food-based products (e.g., beverages, fortified water, energy drinks, nutritional drinks, solid foods, vitamins, supplements, etc.) and pharmaceutical products (e.g., pills, injectable solutions, drugs, etc.). For instance, any one of, any combination of or all of the following ingredients can be included into a food-based or pharmaceutical product: *euterpe oleracea* fruit extract, *punica granatum* sterols, caprooyl tetrapeptide-3, tocopherol or tocopherol acetate, niacinamide, glycerin, and/or *butyrospermum parkii*.

Kits that include the compositions of the present invention are also contemplated. In certain embodiments, the composition is comprised in a container. The container can be a bottle, dispenser, or package. The container can dispense a pre-determined amount of the composition. In certain aspects, the compositions is dispensed in a spray, dollop, or liquid. The container can include indicia on its surface. The indicia can be a word, an abbreviation, a picture, or a symbol.

Also contemplated is a product comprising a composition of the present invention. In non-limiting aspects, the product can be a cosmetic product. The cosmetic product can be those described in other sections of this specification or those known to a person of skill in the art. Non-limiting examples of products include a moisturizer, a cream, a lotion, a skin softener, a foundation, a night cream, a lipstick, a cleanser, a toner, a sunscreen, a mask, an anti-aging product, a deodorant, an antiperspirant, a perfume, a cologne, etc.

It is contemplated that any embodiment discussed in this specification can be implemented with respect to any method or composition of the invention, and vice versa. Furthermore, compositions of the invention can be used to achieve methods of the invention.

In one embodiment, the topical skin compositions of the current invention are pharmaceutically elegant. "Pharmaceutically elegant" describes a composition that has particular tactile properties which feel pleasant on the skin (e.g., compositions that are not too watery or greasy, compositions that have a silky texture, compositions that are non-tacky or sticky, etc.). Pharmaceutically elegant can also relate to the creaminess or lubricity properties of the composition or to the moisture retaining properties of the composition.

"Keratinous tissue" includes keratin-containing layers disposed as the outermost protective covering of mammals and includes, but is not limited to, skin, hair and nails.

"Topical application" means to apply or spread a composition onto the surface of keratinous tissue. "Topical skin composition" includes compositions suitable for topical application on keratinous tissue. Such compositions are typically dermatologically-acceptable in that they do not have undue toxicity, incompatibility, instability, allergic response, and the like, when applied to skin. Topical skin care compositions of the present invention can have a selected viscosity to avoid significant dripping or pooling after application to skin.

The term "about" or "approximately" are defined as being close to as understood by one of ordinary skill in the art, and in one non-limiting embodiment the terms are defined to be within 10%, preferably within 5%, more preferably within 1%, and most preferably within 0.5%.

The terms "inhibiting" or "reducing" or any variation of these terms, when used in the claims and/or the specification includes any measurable decrease or complete inhibition to achieve a desired result.

The term "effective," as that term is used in the specification and/or claims, means adequate to accomplish a desired, expected, or intended result.

The use of the word "a" or "an" when used in conjunction with the term "comprising" in the claims and/or the specification may mean "one," but it is also consistent with the meaning of "one or more," "at least one," and "one or more than one."

The use of the term "or" in the claims is used to mean "and/or" unless explicitly indicated to refer to alternatives only or the alternatives are mutually exclusive, although the disclosure supports a definition that refers to only alternatives and "and/or."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions of the present invention can comprise, consist essentially of, or consist of the claimed ingredients. In one aspect, compositions consisting essentially of the claimed ingredients excludes ingredients that would materially affect a given composition's ability to firm skin, increase the elasticity of skin, stimulate dermal or epidermal cellular activity of skin to increase the connection between the dermal and epidermal layers, reduce or prevent free-radical damage or oxidative damage of skin, moisturize skin, reduce or prevent dry skin or flaky skin, reduce the appearance of fine lines or wrinkles, and/or reduce the appearance of age spots. In another aspect, compositions consisting essentially of dermatologically acceptable vehicles excludes ingredients that would result in undue toxicity, incompatibility, instability, allergic response, and the like, when applied to skin.

Other objects, features and advantages of the present invention will become apparent from the following detailed description. It should be understood, however, that the detailed description and the examples, while indicating specific embodiments of the invention, are given by way of illustration only. Additionally, it is contemplated that changes and modifications within the spirit and scope of the invention will become apparent to those skilled in the art from this detailed description.

DESCRIPTION OF ILLUSTRATIVE EMBODIMENTS

In today's image conscious society, people are continually looking for a product that can improve the visual appearance of their skin. Often times, ageing, chronic exposure to adverse environmental factors, malnutrition, fatigue, etc., can change the visual appearance, physical properties, or physiological functions of skin in ways that are considered visually undesirable.

Typically, cosmetic compositions focus on improving the visual appearance of facial skin at the exclusion of other skin that can be exposed to the same if not more adverse environmental factors. Such skin includes hand skin and skin in the décolleté region (e.g., neck, upper chest, and shoulders), which is oftentimes uncovered by clothing and not protected or treated with topical skin formulations. Combined ultraviolet light and adverse environmental exposure of hand and décolleté skin makes such skin highly susceptible to the visible signs of aging (e.g., loss of skin elasticity, sagging skin, fine lines and wrinkles, age spots, etc.).

Accumulated exposure to UV radiation and environmental pollutants cause the breakdown of healthy collagen fibers and the production of abnormal elastin. Further, ultraviolet (UV) rays can damage melanocytes (skin cells that produce pigment or melanin). Melanocytes, which are located in the skin's epidermis, produce melanin to provide normal skin color. Ultraviolet light exposure triggers the melanocytes to create darker pigment to protect the deeper skin layer, the dermis and the subcutaneous tissue. Once damage occurs, the affected melanocytes may not produce normal skin color. The melanocytes stop producing the normal amount of pigment and create extra pigment. The extra melanin results in random dark spots scattered on the damaged skin (e.g., age spots, which are also referred to as solar lentigines, liver spots, dark spots, brown spots, discolored spots, freckles, etc.). Age spots are collections of melanin in the upper layer of the dermis, and are evidence that free radical damage has occurred. Age spots typically develop in people with a fair complexion but can be seen even in those with darker skin.

The inventors discovered that a unique combination of skin active ingredients, moisturizing agents, and sunscreen agents that can protect and hydrate the skin, revitalize and rebuild the supportive dermal matrix of skin, and reduce uneven pigmentation on the hands and in the décolleté area. When this combination of ingredients is placed in a dermatologically acceptable vehicle, the end result is a topical skin care composition that can treat or prevent a wide range of skin conditions ranging from reduced elasticity, reduced firmness, increased sagginess, dryness, flakiness, fine lines and wrinkles, pits or nodules, damage caused by ultraviolet radiation, age spots, etc. This can be achieved in a single topical skin care composition.

These and other non-limiting aspects of the present invention are described in further detail below.

A. Skin Active Ingredients

Skin active ingredients that can be used in the compositions of the present invention include (but are not limited to) *euterpe oleracea* fruit extract, *punica granatum* extract, caprooyl tetrapeptide-3, tocopherol or tocopherol acetate, and/or niacinamide. In particular aspects, the *punica granatum* extract can include *punica granatum* sterols.

Descriptions of each of these ingredients can be found in the International Cosmetic Ingredient Dictionary and Handbook, 12$^{th}$ Edition (2008) ("CTFA Handbook"), the relevant pages of which are incorporated by reference. Further, the CTFA Handbook also provides a list of companies that supply these ingredients. By way of example, *euterpe oleracea* fruit extract can be obtained from Amax NutraSource (Eugene, Oreg. USA) or Assessa-Industria (Brazil). *Punica granatum* sterols, can be obtained from Active Concepts (Lincolnton, N.C. USA). *Punica granatum* fruit extract, seed extract, pericarp extract are also available for purchase, suppliers of which are listed in the CTFA Handbook. Supplies for tocopherol, tocopherol acetate, and niacinamide are commercially available through a wide range of suppliers. Caprooyl tetrapeptide-3 is a four length amino acid peptide linked to caproic acid. This ingredient is commercially available through Atrium Innovations Inc. (Canada) under the trade name CHRONOLINE™.

For the plant extracts, the inventors contemplate that any part of the plant can be used to make the extract. Non-limiting examples include extracts obtain from the whole plant, leaves, stems, flowers, flower buds, bark, roots, fruit, seeds, and any mixture of such parts. By way of example, the extract can be obtained from the whole fruit (e.g., fruit pulp and seeds), the whole plant (e.g., the entire plant is used to produce the extract), a particular part of the plant at the exclusion of another part (e.g., seed extract isolated from other parts of the plant), etc. The extract can be water-based, alcohol-based, oil-based, gel-based etc.

In addition to purchasing the plant extracts, a person of ordinary skill can also be able to isolate them by using any suitable method known in the art. In one non-limiting example, the whole plant (or any part of the plant—e.g., leaves, stems, bark, roots, fruit, flowers or flower buds, fruit, seeds, seed pods, etc.) can be disrupted by mechanical means which results in a puree. The puree can then be processed to be substantially free of impurities or undesired solids. The puree can then be poured into a shallow vessel and quickly exposed to low temperature, i.e., flash frozen, for example at −20° C. or lower, under a vacuum for removal of water content (lyophilization). The resultant extract can then be used in the compositions of the present invention.

B. Moisturization Agents

The inventors also discovered that a combination of glycerin and *butyrospermum parkii* (shea butter) along with the above mentioned skin actives produces a stable composition having excellent moisturization properties. Both glycerin and *butyrospermum parkii* (shea butter) are described in the CTFA Handbook along with corresponding suppliers of such ingredients. Additional moisturizing ingredients that can be used with the compositions of the present invention are described below.

C. Sunscreen Agents

An additional discovery of the inventors is a combination of sunscreen agents that remain photo-stable when used in combination with the skin actives, moisturizing agents, and dermatologically acceptable vehicle. This allows for a stable and prolonged period of protection from ultraviolet rays after topical application to skin. The following combination works well with the compositions of the present invention: 2-ethylhexyl 2-hydroxybenzoate (also known as octisalate), (2-hydroxy-4-methoxyphenyl)-phenylmethanone (also known as oxybenzone or benzophenone-3), 2-ethylhexyl 2-cyano-3,3-diphenyl-2-propenoate (also known as octocrylene), and 1-(4-methoxyphenyl)-3-(4-tert-butylphenyl)propane-1,3-dione (also known as avobenzone, butylmethoxydibenzoylmethane, or 4-tert-butyl-4'-methoxydibenzoylmethane). Each of these sunscreen agents are described in the CTFA Handbook along with corresponding suppliers of such ingredients.

Additional sunscreen agents that can be used with the compositions of the present invention are described below.

D. Dermatologically Acceptable Vehicle

The aforementioned skin actives, moisturizing agents, and sunscreen agents can be combined in a dermatologically acceptable vehicle, which results in a multi-beneficial composition that remains color stable, photo-stable, and chemically stable. The following combination of ingredients was found to work well with the compositions of the present invention: distearyldimonium chloride; butylene glycol; C12-15 alkyl benzoate; cetyl alcohol; dimethicone; steareth-21; dipropylene glycol dibenzoate; phenoxyethanol; and silica.

The dermatologically acceptable vehicle can be made by simple mixing of the ingredients, while using an appropriate amount of heating to obtain a homogenous mixture. A non-limiting example of such a vehicle is disclosed in the Examples of this specification. Additionally, a person having ordinary skill in the formulations art can use appropriate methods for making a dermatologically acceptable vehicle having the ingredients identified throughout the specification.

E. Compositions of the Present Invention

1. Combinations and Amounts of Ingredients

It is contemplated that the compositions of the present invention can include any one of the skin active ingredients, moisturization agents, sunscreen agents, ingredients in the dermatologically acceptable vehicle, or any combination of these ingredients. The compositions can also include additional ingredients described throughout this specification. The concentrations of the skin actives, moisturization agents, sunscreen agents, ingredients in the dermatologically acceptable vehicle, or any additional ingredients can vary. In non-limiting embodiments, for example, the compositions can include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.1%, 5.2%, 5.3%, 5.4%, 5.5%, 5.6%, 5.7%, 5.8%, 5.9%, 6.0%, 6.1%, 6.2%, 6.3%, 6.4%, 6.5%, 6.6%, 6.7%, 6.8%, 6.9%, 7.0%, 7.1%, 7.2%, 7.3%, 7.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or more, or any range or integer derivable therein, of at least one of, any combination of, or all of the skin actives, ingredients, moisturization agents, sunscreen agents, ingredients in the dermatologically acceptable vehicle, or any additional ingredients disclosed in this specification. In non-limiting aspects, the percentage of such ingredients can be calculated by weight or volume of the total weight of the compositions. The concentrations can vary depending on the desired effect of the compositions or on the product into which the compositions are incorporated.

2. Composition Vehicles

The compositions of the present invention can be formulated into all types of vehicles. Non-limiting examples of suitable vehicles include emulsions (e.g., oil-in-water, water-in-oil, silicone-in-water, water-in-silicone, water-in-oil-in-water, oil-in-water, oil-in-water-in-oil, oil-in-water-in-silicone, etc.), creams, lotions, solutions (both aqueous and hydro-alcoholic), anhydrous bases (such as lipsticks and powders), gels, ointments, pastes, milks, liquids, aerosols, solid forms, or eye jellies. Variations and other appropriate vehicles will be apparent to the skilled artisan and are appropriate for use in the present invention. In certain aspects, the concentrations and combinations of the ingredients can be selected in such a way that the combinations are chemically compatible and do not form complexes which precipitate from the finished product.

It is also contemplated that the skin actives, ingredients, moisturization agents, sunscreen agents, ingredients in the dermatologically acceptable vehicle, or any additional ingredients identified throughout this specification can be encapsulated for delivery to a target area such as skin. Non-limiting examples of encapsulation techniques include the use of liposomes, vesicles, and/or nanoparticles (e.g., biodegradable and non-biodegradable colloidal particles comprising polymeric materials in which the ingredient is trapped, encapsulated, and/or absorbed—examples include nanospheres and nanocapsules) that can be used as delivery vehicles to deliver such ingredients to skin (see, e.g., U.S. Pat. No. 6,387,398; U.S. Pat. No. 6,203,802; U.S. Pat. No. 5,411,744; Kreuter 1988).

3. Products

The compositions of the present invention can be incorporated into cosmetic products, food-based products (e.g., fortified water, energy drinks, nutritional drinks, vitamins, supplements, solid foods), pharmaceutical products, etc. Non-limiting examples of cosmetic products include hand treatment products, décolleté treatment products, sunless skin tanning products, hair products (e.g., shampoos, conditioners, colorants, dyes, bleaches, straighteners, and permanent wave products), fingernail products, moisturizing creams, skin creams and lotions, softeners, day lotions, gels, ointments, foundations, night creams, lipsticks and lip balms, cleansers, toners, masks, deodorants, antiperspirants, exfoliating compositions, shaving-related products (e.g., creams, "bracers" and aftershaves), pre-moistened wipes and washcloths, tanning lotions, bath products such as oils, foot care products such as powders and sprays, skin colorant and make-up products such as foundations, blushes, rouges eye shadows and lines, lip colors and mascaras, baby products (e.g., baby lotions, oils, shampoos, powders and wet wipes), and skin or facial peel products. Additionally, the cosmetic products can be formulated as leave-on or rinse-off products.

4. Additional Ingredients

Compositions of the present invention can include additional ingredients. Non-limiting examples of additional ingredients include cosmetic ingredients (both active and non-active) and pharmaceutical ingredients (both active and non-active).

a. Cosmetic Ingredients

The CTFA Handbook describes a wide variety of non-limiting cosmetic ingredients that can be used in the context of the present invention. Examples of these ingredient classes include: fragrances (artificial and natural), dyes and color ingredients (e.g., Blue 1, Blue 1 Lake, Red 40, titanium dioxide, D&C blue no. 4, D&C green no. 5, D&C orange no. 4, D&C red no. 17, D&C red no. 33, D&C violet no. 2, D&C yellow no. 10, and D&C yellow no. 11), adsorbents, emulsifiers, stabilizers, lubricants, solvents, moisturizers (including, e.g., emollients, humectants, film formers, occlusive agents, and agents that affect the natural moisturization mechanisms of the skin), water-repellants, UV absorbers (physical and chemical absorbers such as paraaminobenzoic acid ("PABA") and corresponding PABA derivatives, titanium dioxide, zinc oxide, etc.), essential oils, vitamins (e.g., A, B, C, D, E, and K), trace metals (e.g., zinc, calcium and selenium), anti-irritants (e.g., steroids and non-steroidal anti-inflammatories), botanical extracts (e.g., aloe vera, chamomile, cucumber extract, *ginkgo biloba*, ginseng, and rosemary), anti-microbial agents, antioxidants (e.g., BHT), chelating agents (e.g., disodium EDTA and tetrasodium EDTA), preservatives (e.g., methylparaben and propylparaben), pH adjusters (e.g., sodium hydroxide and citric acid), absorbents (e.g., aluminum starch octenylsuccinate, kaolin, corn starch, oat starch, cyclodextrin, talc, and zeolite), skin bleaching and lightening agents (e.g., hydroquinone and niacinamide lactate), humectants (e.g., propylene glycol, butylene glycol, pentylene glycol, sorbitol, urea, and manitol), exfoliants (e.g., alpha-hydroxyacids, and beta-hydroxyacids such as lactic acid, glycolic acid, and salicylic acid; and salts thereof) waterproofing agents (e.g., magnesium/aluminum hydroxide stearate), skin conditioning agents (e.g., aloe extracts, allantoin, bisabolol, ceramides, dimethicone, hyaluronic acid, and dipotassium glycyrrhizate), thickening agents (e.g., substances which that can increase the viscosity of a composition such as carboxylic acid polymers, crosslinked polyacrylate polymers, polyacrylamide polymers, polysaccharides, and gums), and silicone containing compounds (e.g., silicone oils and polyorganosiloxanes). The following provides specific non-limiting examples of some of the additional ingredients that can be used with the compositions of the present invention.

i. Additional Sunscreen Agents

UV absorption agents that can be used in combination with the compositions of the present invention include chemical and physical sunblocks. Non-limiting examples of chemical sunblocks that can be used include para-aminobenzoic acid (PABA), PABA esters (glyceryl PABA, amyldimethyl PABA and octyldimethyl PABA), butyl PABA, ethyl PABA, ethyl dihydroxypropyl PABA, benzophenones (oxybenzone, sulisobenzone, benzophenone, and benzophenone-1 through 12), cinnamates (octyl methoxycinnamate, isoamyl p-methoxycinnamate, octylmethoxy cinnamate, cinoxate, diisopropyl methyl cinnamate, DEA-methoxycinnamate, ethyl diisopropylcinnamate, glyceryl octanoate dimethoxycinnamate and ethyl methoxycinnamate), cinnamate esters, salicylates (homomethyl salicylate, benzyl salicylate, glycol salicylate, isopropylbenzyl salicylate, etc.), anthranilates, ethyl urocanate, homosalate, octisalate, dibenzoylmethane derivatives, octyl triazone, digalloy trioleate, glyceryl aminobenzoate, lawsone with dihydroxyacetone, ethylhexyl triazone, dioctyl butamido triazone, benzylidene malonate polysiloxane, terephthalylidene dicamphor sulfonic acid, disodium phenyl dibenzimidazole tetrasulfonate, diethylamino hydroxybenzoyl hexyl benzoate, bis diethylamino hydroxybenzoyl benzoate, bis benzoxazoylphenyl ethylhexylimino triazine, drometrizole trisiloxane, methylene bis-benzotriazolyl tetramethylbutylphenol, and bis-ethylhexyloxyphenol methoxyphenyltriazine, 4-methylbenzylidenecamphor, and isopentyl 4-methoxycinnamate. Non-limiting examples of physical sunblocks include, kaolin, talc, petrolatum and metal oxides (e.g., titanium dioxide and zinc oxide). Compositions of the present invention can have UVA and UVB absorption properties. The compositions can have an sun protection factor (SPF) of 2, 3, 4, 56, 7, 8, 9, 10, 11, 12, 13, 14, 15, 20, 25, 30, 35, 40, 45, 50, 55, 60, 70, 80, 90 or more, or any integer or derivative therein.

ii. Additional Moisturizing Agents

Non-limiting examples of moisturizing agents that can be used with the compositions of the present invention include amino acids, chondroitin sulfate, diglycerin, erythritol, fructose, glucose, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C10-30 alkyl acrylate crosspolymer, acrylates copolymer, alanine, algae extract, aloe barbadensis, aloe-barbadensis extract, aloe barbadensis gel, althea officinalis extract, aluminum starch octenylsuccinate, aluminum stearate, apricot (*prunus armeniaca*) kernel oil, arginine, arginine aspartate, *arnica montana* extract, ascorbic acid, ascorbyl palmitate, aspartic acid, avocado (*persea gratissima*) oil, barium sulfate, barrier sphingolipids, butyl alcohol, beeswax, behenyl alcohol, beta-sitosterol, BHT, birch (*betula alba*) bark extract, borage (*borago officinalis*) extract, 2-bromo-2-nitropropane-1,3-diol, butcherbroom (*ruscus aculeatus*) extract, butylene glycol, *calendula officinalis* extract, *calendula officinalis* oil, candelilla (*euphorbia cerifera*) wax, canola oil, caprylic/capric triglyceride, *cardamon (elettaria cardamomum)* oil, carnauba (*copernicia cerifera*) wax, carrageenan (*chondrus crispus*), carrot (*daucus carota sativa*) oil, castor (*ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*anthemis nobilis*) oil, cholesterol, cholesterol esters, cholesteryl hydroxystearate, citric acid, clary (*salvia sclarea*) oil, cocoa (*theobroma cacao*) butter, coco-caprylate/caprate, coconut (*cocos nucifera*) oil, collagen, collagen amino acids, corn (*zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, eucalyptus globulus oil, evening primrose (*oenothera biennis*) oil, fatty acids, tructose, gelatin, *geranium maculatum* oil, glucosamine, glucose glutamate, glutamic acid, glycereth-26, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*vitis vinifera*) seed oil, hazel (*corylus americana*) nut oil, hazel (*corylus avellana*) nut oil, hexylene glycol, honey, hyaluronic acid, hybrid safflower (*carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*jasminum officinale*) oil, jojoba (*buxus chinensis*) oil, kelp, kukui (*aleurites moluccana*) nut oil, lactamide MEA, laneth-16, laneth-10 acetate, lanolin, lanolin acid, lanolin alcohol, lanolin oil, lanolin wax, lavender (*lavandula angustifolia*) oil, lecithin, lemon (*citrus medica limonum*) oil, linoleic acid, linolenic acid, *macadamia ternifolia* nut oil, magnesium stearate, magnesium sulfate, maltitol, matricaria (*chamomilla recutita*) oil, methyl glucose sesquistearate, methylsilanol PCA, microcrystalline wax, mineral oil, mink oil, *mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*olea europaea*) oil, orange (*citrus aurantium dulcis*) oil, palm (*elaeis guineensis*) oil, palmitic acid, pantethine, panthenol, panthenyl ethyl ether, paraffin, PCA, peach (*prunus persica*) kernel oil, peanut (*arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*oryza sativa*) bran oil, RNA, rosemary (*rosmarinus officinalis*) oil, rose oil, safflower (*carthamus tinctorius*) oil, sage (*salvia officinalis*) oil, salicylic acid, sandalwood (*santalum album*) oil, serine, serum protein, sesame (*sesamum indicum*) oil, silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*helianthus annuus*) seed oil, sweet almond (*prunus amygdalus dulcis*) oil, synthetic beeswax, tocopheryl linoleate, tribehenin, tridecyl neopentanoate, tridecyl stearate, triethanolamine, tristearin, urea, vegetable oil, water, waxes, wheat (*triticum vulgare*) germ oil, and ylang ylang (*cananga odorata*) oil.

iii. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfate, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl linoleate, tocopheryl nicotinate, tocopheryl succinate, and tris(nonylphenyl)phosphite.

iv. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

v. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

vi. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O— chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In preferred aspects, the silicon containing compounds includes a silicone oils such as a polyorganosiloxane. Non-limiting examples of polyorganosiloxanes include dimethicone, cyclomethicone, polysilicone-11, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 cst or less (e.g., dimethicones such as Dow Corning 200-0.5 cst Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Mich.

vii. Essential Oils

Essential oils include oils derived from herbs, flowers, trees, and other plants. Such oils are typically present as tiny droplets between the plant's cells, and can be extracted by several method known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (vegetal), and other organic solvents. Typical physical characteristics found in essential oils include boiling points that vary from about 160° to 240° C. and densities ranging from about 0.759 to about 1.096.

Essential oils typically are named by the plant from which the oil is found. For example, rose oil or peppermint oil are derived from rose or peppermint plants, respectively. Non-limiting examples of essential oils that can be used in the context of the present invention include sesame oil, *macadamia* nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

viii. Thickening Agents

Thickening agents, including thickener or gelling agents, include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053; CTFA International Cosmetic Ingredient Dictionary, $4^{th}$ Ed., 1991). Examples of commercially available carboxylic acid polymers include carbomers, which are homopolymers of acrylic acid crosslinked with allyl ethers of sucrose or pentaerytritol (e.g., Carbopol™ 900 series from B. F. Goodrich).

Non-limiting examples of crosslinked polyacrylate polymers include cationic and nonionic polymers. Examples are described in U.S. Pat. Nos. 5,100,660; 4,849,484; 4,835,206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (preferably hydroxy ethylated or hydroxypropylated) to form a hydroxyalkylated cellulose which is then further modified with a $C_{10}$-$C_{30}$ straight chain or branched chain alkyl group through an ether linkage. Typically these polymers are ethers of $C_{10}$-$C_{30}$ straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

b. Pharmaceutical Ingredients

Pharmaceutical ingredients are also contemplated as being useful with the emulsion compositions of the present invention. Non-limiting examples of pharmaceutical ingredients include anti-acne agents, agents used to treat rosacea, analgesics, anesthetics, anorectals, antihistamines, anti-inflammatory agents including non-steroidal anti-inflammatory drugs, antibiotics, antifungals, antivirals, antimicrobials, anti-cancer actives, scabicides, pediculicides, antineoplastics, antiperspirants, antipruritics, antipsoriatic agents, antiseborrheic agents, biologically active proteins and peptides, burn treatment agents, cauterizing agents, depigmenting agents, depilatories, diaper rash treatment agents, enzymes, hair growth stimulants, hair growth retardants including DFMO and its salts and analogs, hemostatics, kerotolytics, canker sore treatment agents, cold sore treatment agents, dental and periodontal treatment agents, photosensitizing actives, skin protectant/barrier agents, steroids including hormones and corticosteroids, sunburn treatment agents, sunscreens, transdermal actives, nasal actives, vaginal actives, wart treatment agents, wound treatment agents, wound healing agents, etc.

F. Kits

Kits are also contemplated as being used in certain aspects of the present invention. For instance, a composition of the present invention can be included in a kit. A kit can include a container. Containers can include a bottle, a metal tube, a laminate tube, a plastic tube, a dispenser, a pressurized container, a barrier container, a package, a compartment, a lipstick container, a compact container, cosmetic pans that can hold cosmetic compositions, or other types of containers such as injection or blow-molded plastic containers into which the dispersions or compositions or desired bottles, dispensers, or packages are retained. The kit and/or container can include indicia on its surface. The indicia, for example, can be a word, a phrase, an abbreviation, a picture, or a symbol.

The containers can dispense a pre-determined amount of a composition. In other embodiments, the container can be squeezed (e.g., metal, laminate, or plastic tube) to dispense a desired amount of the composition. The composition can be dispensed as a spray, foam, an aerosol, a liquid, a fluid, or a semi-solid. The containers can have spray, pump, or squeeze mechanisms. A kit can also include instructions for using the kit and/or compositions. Instructions can include an explanation of how to apply, use, and maintain the compositions.

EXAMPLES

The following examples are included to demonstrate certain non-limiting aspects of the invention. It should be appreciated by those of skill in the art that the techniques disclosed in the examples which follow represent techniques discovered by the inventors to function well in the practice of the invention. However, those of skill in the art should, in light of the present disclosure, appreciate that many changes can be made in the specific embodiments which are disclosed and still obtain a like or similar result without departing from the spirit and scope of the invention.

Example 1

Testing Vehicles and Compositions

Tables 1 and 2 describe generic skin testing formulations in which a skin active ingredient, moisturizing ingredient, or sunscreen agent can be incorporated into to determine the types of skin benefits that can be attributed to such ingredients. These formulations are prepared in such a manner that any resulting skin benefit from topical application of the formula to skin can be directly attributed to the ingredients being tested.

TABLE 1*

| Ingredient | % Concentration (by weight) |
| --- | --- |
| Phase A | |
| Water | q.s. |
| Xanthum gum | 0.1 |
| M-paraben | 0.15 |
| P-paraben | 0.1 |
| Citric acid | 0.1 |
| Phase B | |
| Cetyl alcohol | 4.0 |
| Glyceryl stearate + PEG 100 | 4.0 |
| Octyl palmitate | 4.0 |
| Dimethicone | 1.0 |
| Tocopheryl acetate | 0.2 |
| Phase C** | |
| Test Ingredient(s) | 2.0 |
| TOTAL | 100 |

*Procedure for making composition: Sprinkle Xanthum gum in water and mix for 10 min. Subsequently, add all ingredients in phase A and heat to 70-75° C. Add all items in phase B to separate beaker and heat to 70-75° C. Mix phases A and B at 70-75° C. Continue mixing and allow composition to cool to 30° C. Subsequently, add phase C ingredient while mixing.
**The test ingredient(s) can be those described throughout this specification (e.g., skin active, moisturization agent, sunscreen agent, etc.). Such ingredients can be individually used or combined in this testing vehicle. The concentration ranges of the ingredients can be modified as desired or needed by increasing or decreasing the amount of water. For instance, the skin active ingredients can include *euterpe oleracea* fruit extract, *punica granatum* sterols, caprooyl tetrapeptide-3, tocopherol or tocopherol acetate, or niacinamide, or any combination thereof. The moisturizing agents can include glycerin or *butyrospermum parkii* or both. The sunscreen agents can include 2-ethylhexyl 2-hydroxybenzoate, 2-hydroxy-4-methoxyphenyl)-phenylmethanone, 2-ethylhexyl 2-cyano-3,3-diphenyl-2-propenoate, or 1-(4-methoxyphenyl)-3-(4-tert-butylphenyl)propane-1,3-dione, or any combination thereof. With respect to plant extracts (e.g., *euterpe oleracea* and *punica granatum*), any portion of the plant can be used for testing (e.g., root, stem, leaf, flower, flower bulb, bark, fruit, seed, seed pod, whole plant etc.).

TABLE 2*

| Ingredient | % Concentration (by weight) |
| --- | --- |
| Phase A | |
| Water | q.s. |
| M-paraben | 0.2 |
| P-paraben | 0.1 |
| Na2 EDTA | 0.1 |
| Shea butter | 4.5 |
| Petrolatum | 4.5 |
| Glycerin | 4.0 |
| Propylene Glycol | 2.0 |
| Finsolve TN | 2.0 |

TABLE 2*-continued

| Ingredient | % Concentration (by weight) |
|---|---|
| Phase B | |
| Sepigel 305 | 2.0 |
| Phase C** | |
| Test Ingredient(s) | 2.0 |
| TOTAL | 100 |

*Add ingredients in phase A to beaker and heat to 70-75° C while mixing. Subsequently, add the phase B ingredient with phase A and cool to 30° C. with mixing. Subsequently, add phase C ingredient while mixing.
**The test ingredient(s) can be those described throughout this specification (e.g., skin active, moisturization agent, sunscreen agent, etc.). Such ingredients can be individually used or combined in this testing vehicle. The concentration ranges of the ingredients can be modified as desired or needed by increasing or decreasing the amount of water. For instance, the skin active ingredients can include euterpe oleracea fruit extract, punica granatum sterols, caprooyl tetrapeptide-3, tocopherol or tocopherol acetate, or niacinamide, or any combination thereof. The moisturizing agents can include glycerin or butyrospermum parkii or both. The sunscreen agents can include 2-ethylhexyl 2-hydroxybenzoate, 2-hydroxy-4-methoxyphenyl)-phenylmethanone, 2-ethylhexyl 2-cyano-3,3-diphenyl-2-propenoate, or 1-(4-methoxyphenyl)-3-(4-tert-butylphenyl)propane-1,3-dione, or any combination thereof. With respect to plant extracts (e.g., euterpe oleracea and punica granatum), any portion of the plant can be used for testing (e.g., root, stem, leaf, flower, flower bulb, bark, fruit, seed, seed pod, whole plant etc.).

The formulations represented in Tables 3-4 are non-limiting examples of the types of compositions that can be used in the context of the present invention. Any standard method can be used to prepare such compositions. For instance, simple mixing of the ingredients in a beaker can be used. One should mix such ingredients and add heat as necessary to obtain a homogenous composition.

The Table 3 composition can be formulated into a cream, and the additional ingredients identified throughout the specification can be included into the Table 3 composition (e.g., by adjusting the water content of composition). Further, the concentration ranges of the ingredients identified in Table 3 can vary depending on a desired formulation (e.g., cream, lotion, moisturizer, cleanser, etc.).

TABLE 3*

| Ingredient | % Concentration (by weight) |
|---|---|
| Skin Active Ingredients** | 1 to 3% |
| Skin Moisturization Agents** | 5 to 15% |
| Sunscreen Agents* | 10 to 15% |
| Odor Neutralizing Agents*** | 0.02 to 0.5% |
| Dermatologically Acceptable Vehicle | |
| Water | q.s. (at least 50%) |
| Distearyldimonium Chloride | 2 to 5% |
| Butylene Glycol | 2 to 5% |
| C12-15 Alkyl Benzoate | 1 to 3% |
| Cetyl Alcohol | 1 to 3% |
| Dimethicone | 0.1 to 2% |
| Steareth-21 | 0.1 to 2% |
| Dipropylene Glycol Dibenzoate | 0.1 to 2% |
| Phenoxyethanol | 0.1 to 2% |
| Silica | 0.1 to 2% |
| TOTAL | 100 |

*The composition can be made by using simple mixing procedures. The ingredients can be added to a beaker and heated to 70-75° C. while mixing. Subsequently, the mixture can be cooled to room temperature with constant mixing. Mixing can be stopped once a homogenous composition is obtained.
**The skin active ingredients include euterpe oleracea fruit extract, punica granatum sterols, caprooyl tetrapeptide-3, tocopherol or tocopherol acetate, and niacinamide. The moisturizing agents include glycerin and butyrospermum parkii. The sunscreen agents include 2-ethylhexyl 2-hydroxybenzoate, 2-hydroxy-4-methoxyphenyl)-phenylmethanone, 2-ethylhexyl 2-cyano-3,3-diphenyl-2-propenoate, and 1-(4-methoxyphenyl)-3-(4-tert-butylphenyl)propane-1,3-dione.
***The odor neutralizing agents can be used to mask the smell of the formulation. Use of such ingredients can be used to produce a formulation that has no discernable odor (e.g., a fragrance-free formulation), such as the one exhibited in Table 3.

The Table 4 composition can be formulated into a cream, and the additional ingredients identified throughout the specification can be included into the Table 4 composition (e.g., by adjusting the water content of composition). Further, the concentration ranges of the ingredients identified in Table 4 can vary depending on a desired formulation (e.g., cream, lotion, moisturizer cleanser, etc.).

TABLE 4*

| Ingredient | % Concentration (by weight) |
|---|---|
| Water | q.s. |
| Glycerin | 3-7 |
| Octisalate | 2-5 |
| Distearyldimonium Chloride | 1-5 |
| Oxybenzone | 1-5 |
| Butylene Glycol | 1-5 |
| Octocrylene | 1-5 |
| C12-15 Alkyl Benzoate | 1-5 |
| Cetyl Alcohol | 1-5 |
| Avobenzone | 1-5 |
| Butyrospermum Parkii (Shea Butter) | 1-5 |
| Dimethicone | 1-5 |
| Steareth-21 | 0.1 to 2 |
| Niacinamide | 0.1 to 2 |
| Dipropylene Glycol Dibenzoate | 0.1 to 2 |
| Phenoxyethanol | 0.1 to 2 |
| Tocopheryl Acetate | 0.1 to 2 |
| Punica Granatum Sterols | 0.1 to 2 |
| Silica | 0.1 to 2 |
| PPG-15 Stearyl Ether Benzoate | 0.1 to 2 |
| Methylparaben | 0.1 to 2 |
| Hydrogenated Lecithin | 0.1 to 2 |
| Disodium EDTA | 0.01 to 1 |
| Ethylene Brassylate | 0.01 to 1 |
| Ethylparaben | 0.01 to 1 |
| Sodium Chloride | 0.01 to 1 |
| Propylparaben | 0.01 to 1 |
| Triethanolamine | 0.01 to 1 |
| Euterpe Oleracea Fruit Extract | 0.001 to 0.1 |
| Isobutyl Methyl Tetrahydropyranol | 0.001 to 0.1 |
| Methyl Linalool | 0.001 to 0.1 |
| Methylenedioxyphenyl Methylpropanal | 0.001 to 0.1 |
| Phenylisohexanol | 0.001 to 0.1 |
| Cyclamen Aldehyde | 0.001 to 0.1 |
| Caprooyl Tetrapeptide-3 | 0.0001-0.001 |
| TOTAL | 100 |

*The composition can be made by using simple mixing procedures. The ingredients can be added to a beaker and heated to 70-75° C. while mixing. Subsequently, the mixture can be cooled to room temperature with constant mixing. Mixing can be stopped once a homogenous composition is obtained.

Example 2

Efficacy

The efficacy of a composition having the parameters identified in Tables 3 and 4 is summarized below in the following Table 5.

TABLE 5*

| Panelist Question | Two Weeks of Use | Four Weeks of Use | Eight Weeks of Use |
|---|---|---|---|
| Softens the Appearance of Crepiness | 80% (yes) | DNR* | DNR |
| Firmer Skin | DNR | 80% (yes) | 85% (yes) |
| Reduced Appearance of Fine Lines | DNR | 78% (yes) | DNR |
| Reduced Appearance of Wrinkles | DNR | DNR | 80% (yes) |
| Reduced Appearance of Age Spots | DNR | DNR | 60% (yes) |

*Results reported during an independent consumer study, in which 125 women used the Table 4 formulation twice/day for an 8 week period.
**DNR is data not requested in survey.

Example 3

Additional Assays that Can be Used to Test Compositions

The efficacy of the compositions of the present invention can be determined by methods known to those of ordinary skill in the art. The following are non-limiting assays that can be used in the context of the present invention. It should be recognized that other testing procedures can be used, including, for example, objective and subjective procedures.

Skin Firmness and Elasticity Assay with a Hargens Ballistometer: Skin firmness and elasticity can be measured using a Hargens ballistometer, a device that evaluates the firmness and elasticity of the skin by dropping a small body onto the skin and recording its first two rebound peaks. The ballistometry is a small lightweight probe with a relatively blunt tip (4 square mm-contact area) was used. The probe penetrates slightly into the skin and results in measurements that are dependent upon the properties of the outer layers of the skin, including the stratum corneum and outer epidermis and some of the dermal layers.

Skin Softness/Suppleness Assay with a Gas Bearing Electrodynamometer: Skin softness/suppleness can be evaluated using the Gas Bearing Electrodynamometer, an instrument that measures the stress/strain properties of the skin. The viscoelastic properties of skin correlate with skin moisturization. Measurements can be obtained on the predetermined site on the cheek area by attaching the probe to the skin surface with double-stick tape. A force of approximately 3.5 gm can be applied parallel to the skin surface and the skin displacement is accurately measured. Skin suppleness can then be calculated and is expressed as DSR (Dynamic Spring Rate in gm/mm).

Skin Moisture/Hydration Assay: Skin moisture/hydration benefits can be measured by using impedance measurements with the Nova Dermal Phase Meter. The impedance meter measures changes in skin moisture content. The outer layer of the skin has distinct electrical properties. When skin is dry it conducts electricity very poorly. As it becomes more hydrated increasing conductivity results. Consequently, changes in skin impedance (related to conductivity) can be used to assess changes in skin hydration. The unit can be calibrated according to instrument instructions for each testing day. A notation of temperature and relative humidity can also be made. Subjects can be evaluated as follows: prior to measurement they can equilibrate in a room with defined humidity (e.g., 30-50%) and temperature (e.g., 68-72° C.). Three separate impedance readings can be taken on each side of the face, recorded, and averaged. The T5 setting can be used on the impedance meter which averages the impedance values of every five seconds application to the face. Changes can be reported with statistical variance and significance.

Skin Dryness, Surface Lines, Skin Smoothness, and Skin Tone Assay: Skin dryness, surface fine lines, skin smoothness, and skin tone can be evaluated with clinical grading techniques. For example, clinical grading of skin dryness can be determined by a five point standard Kligman Scale: (0) skin is soft and moist; (1) skin appears normal with no visible dryness; (2) skin feels slightly dry to the touch with no visible flaking; (3) skin feels dry, tough, and has a whitish appearance with some scaling; and (4) skin feels very dry, rough, and has a whitish appearance with scaling. Evaluations can be made independently by two clinicians and averaged.

Skin Smoothness and Wrinkle Reduction Assay With Methods Disclosed in Packman et al. (1978): Skin smoothness and wrinkle reduction can also be assessed visually by using the methods disclosed in Packman and Gams (1978). For example, at each subject visit, the depth, shallowness and the total number of superficial facial lines (SFLs) of each subject can be carefully scored and recorded. A numerical score was obtained by multiplying a number factor times a depth/width/length factor. Scores are obtained for the eye area and mouth area (left and right sides) and added together as the total wrinkle score.

Appearance of Lines and Wrinkles Assay with Replicas: The appearance of lines and wrinkles on the skin can be evaluated using replicas, which is the impression of the skin's surface. Silicone rubber like material can be used. The replica can be analyzed by image analysis. Changes in the visibility of lines and wrinkles can be objectively quantified via the taking of silicon replicas form the subjects' face and analyzing the replicas image using a computer image analysis system. Replicas can be taken from the eye area and the neck area, and photographed with a digital camera using a low angle incidence lighting. The digital images can be analyzed with an image processing program and the are of the replicas covered by wrinkles or fine lines was determined.

Surface Contour of the Skin Assay with a Profilometer/Stylus Method: The surface contour of the skin can be measured by using the profilometer/Stylus method. This includes either shining a light or dragging a stylus across the replica surface. The vertical displacement of the stylus can be fed into a computer via a distance transducer, and after scanning a fixed length of replica a cross-sectional analysis of skin profile can be generated as a two-dimensional curve. This scan can be repeated any number of times along a fix axis to generate a simulated 3-D picture of the skin. Ten random sections of the replicas using the stylus technique can be obtained and combined to generate average values. The values of interest include Ra which is the arithmetic mean of all roughness (height) values computed by integrating the profile height relative to the mean profile height. Rt which is the maximum vertical distance between the highest peak and lowest trough, and Rz which is the mean peak amplitude minus the mean peak height. Values are given as a calibrated value in mm. Equipment should be standardized prior to each use by scanning metal standards of know values. Ra Value can be computed by the following equation: $R_a$=Standardize roughness; $l_m$=the traverse (scan) length; and y=the absolute value of the location of the profile relative to the mean profile height (x-axis).

Skin Clarity and Reduction in Freckles and Age Spots Assay: Skin clarity and the reduction in freckles and age spots can be evaluated using a Minolta Chromometer. Changes in skin color can be assessed to determine irritation potential due to product treatment using the a* values of the Minolta Chroma Meter. The a* value measures changes in skin color in the red region. This is used to determine whether a composition is inducing irritation. The measurements can be made on each side of the face and averaged, as left and right facial values. Skin clarity can also be measured using the Minolta Meter. The measurement is a combination of the a*, b, and L values of the Minolta Meter and is related to skin brightness, and correlates well with skin smoothness and hydration. Skin reading is taken as above. In one non-limiting aspect, skin clarity can be described as L/C where C is chroma and is defined as $(a^2+b^2)^{1/2}$ All of the skin-active ingredients, compositions, or methods disclosed and claimed in this specification can be made and executed without undue experimentation in light of the present disclosure. While the skin-active ingredients, compositions, or methods of this invention have been described in terms of particular embodiments, it will be apparent to those of skill in the art that variations may be applied to the skin-active ingredients, compositions, or methods and in the steps or in the sequence of steps of the method described herein without departing from the concept, spirit and scope of the invention.

REFERENCES

Any one of the references identified in the specification, to the extent that they provide exemplary procedural or other details supplementary to those set forth in this specification, are specifically incorporated by reference.

The invention claimed is:

1. A topical skin care composition consisting of:
water;
glycerin;
2-ethylhexyl 2-hydroxybenzoate;
distearyldimonium chloride;
2-hydroxy-4-methoxyphenyl-phenylmethanone;
butylene glycol;
2-ethylhexyl 2-cyano-3,3-diphenyl-2-propenoate;
C12-15 alkyl benzoate;
cetyl alcohol;
1-(4-methoxyphenyl)-3-(4-tert-butylphenyl)propane-1,3-dione;
*butyrospermum parkii;*
dimethicone;
steareth-21;
niacinamide;
dipropylene glycol dibenzoate;
phenoxyethanol;
tocopherol or tocopherol acetate;
*punica granatum* sterols;
silica;
PPG-15 stearyl ether benzoate;
methylparaben;
hydrogenated lecithin;
disodium EDTA;
ethylene brassylate;
ethylbaraben;
sodium chloride;
propylparaben;
triethanolamine;
*euterpe oleracea* fruit extract;
isobutyl methyl tetrahydropyranol;
methyl linalool;
methylenedioxyphenyl methylpropanal;
phenylisohexanol;
cyclamen aldehyde; and
caprooyl tetrapeptide-3.

2. The topical skin care composition of claim 1 consisting of:
60-65% w/w of water;
3-7% w/w of glycerin;
3-7% w/w of 2-ethylhexyl 2-hydroxybenzoate;
2-5% w/w of distearyldimonium chloride;
2-4% w/w of 2-hydroxy-4-methoxyphenyl-phenylmethanone;
2 to 5% w/w of butylene glycol;
1-3% w/w of 2-ethylhexyl 2-cyano-3,3-diphenyl-2-propenoate;
1 to 3% w/w of C12-15 alkyl benzoate;
1 to 3% w/w of cetyl alcohol;
1 to 3% w/w of 1-(4-methoxyphenyl)-3-(4-tert-butylphenyl)propane-1,3-dione;
1 to 3% w/w of *butyrospermum parkii;*
1 to 2% w/w of dimethicone;
0.1 to 2% w/w of steareth-21;
0.1 to 2% w/w of niacinamide;
0.1 to 2% w/w of dipropylene glycol dibenzoate;
0.1 to 2% w/w of phenoxyethanol;
0.1 to 1% w/w of tocopherol or tocopherol acetate;
0.1 to 1% w/w of *punica granatum* sterols;
0.1 to 2% w/w of silica;
0.01 to 0.2% w/w of PPG-15 stearyl ether benzoate;
0.01 to 0.2% w/w of methylparaben;
0.01 to 0.2% w/w of hydrogenated lecithin;
0.01 to 0.2% w/w of disodium EDTA;
0.01 to 0.2% w/w of ethylene brassylate;
0.01 to 0.2% w/w of ethylbaraben;
0.01 to 0.2% w/w of sodium chloride;
0.01 to 0.2% w/w of propylparaben;
0.01 to 0.2% w/w of triethanolamine;
0.001 to 0.2% w/w of *euterpe oleracea;*
0.001 to 0.2% w/w of isobutyl methyl tetrahydropyranol;
0.001 to 0.2% w/w of methyl linalool;
0.001 to 0.2% w/w of methylenedioxyphenyl methylpropanal;
0.001 to 0.2% w/w of phenylisohexanol;
0.001 to 0.2% w/w of cyclamen aldehyde; and
0.0001 to 0.2% w/w of caprooyl tetrapeptide-3.

3. A topical skin care composition comprising:
water;
glycerin;
2-ethylhexyl 2-hydroxybenzoate;
distearyldimonium chloride;
2-hydroxy-4-methoxyphenyl-phenylmethanone;
butylene glycol;
2-ethylhexyl 2-cyano-3,3-diphenyl-2-propenoate;
C12-15 alkyl benzoate;
cetyl alcohol;
1-(4-methoxyphenyl)-3-(4-tert-butylphenyl)propane-1,3-dione;
*butyrospermum parkii;*
dimethicone;
steareth-21;
niacinamide;
dipropylene glycol dibenzoate;
phenoxyethanol;
tocopherol or tocopherol acetate;
*punica granatum* sterols;
silica;
PPG-15 stearyl ether benzoate;
methylparaben;
hydrogenated lecithin;
disodium EDTA;
ethylene brassylate;
ethylbaraben;
sodium chloride;
propylparaben;
triethanolamine;
*euterpe oleracea* fruit extract;
isobutyl methyl tetrahydropyranol;
methyl linalool;
methylenedioxyphenyl methylpropanal;
phenylisohexanol;
cyclamen aldehyde; and
caprooyl tetrapeptide-3.

4. The topical skin care composition of claim 1 comprising:
60-65% w/w of water;
3-7% w/w of glycerin;
3-7% w/w of 2-ethylhexyl 2-hydroxybenzoate;
2-5% w/w of distearyldimonium chloride;

2-4% w/w of 2-hydroxy-4-methoxyphenyl-phenylmethanone;
2 to 5% w/w of butylene glycol;
1-3% w/w of 2-ethylhexyl 2-cyano-3,3-diphenyl-2-propenoate;
1 to 3% w/w of C12-15 alkyl benzoate;
1 to 3% w/w of cetyl alcohol;
1 to 3% w/w of 1-(4-methoxyphenyl)-3-(4-tert-butylphenyl)propane-1,3-dione;
1 to 3% w/w of *butyrospermum parkii*;
1 to 2% w/w of dimethicone;
0.1 to 2% w/w of steareth-21;
0.1 to 2% w/w of niacinamide;
0.1 to 2% w/w of dipropylene glycol dibenzoate;
0.1 to 2% w/w of phenoxyethanol;
0.1 to 1% w/w of tocopherol or tocopherol acetate;
0.1 to 1% w/w of *punica granatum* sterols;
0.1 to 2% w/w of silica;
0.01 to 0.2% w/w of PPG-15 stearyl ether benzoate;
0.01 to 0.2% w/w of methylparaben;
0.01 to 0.2% w/w of hydrogenated lecithin;
0.01 to 0.2% w/w of disodium EDTA;
0.01 to 0.2% w/w of ethylene brassylate;
0.01 to 0.2% w/w of ethylbaraben;
0.01 to 0.2% w/w of sodium chloride;
0.01 to 0.2% w/w of propylparaben;
0.01 to 0.2% w/w of triethanolamine;
0.001 to 0.2% w/w of *euterpe oleracea*;
0.001 to 0.2% w/w of isobutyl methyl tetrahydropyranol;
0.001 to 0.2% w/w of methyl linalool;
0.001 to 0.2% w/w of methylenedioxyphenyl methylpropanal;
0.001 to 0.2% w/w of phenylisohexanol;
0.001 to 0.2% w/w of cyclamen aldehyde; and
0.0001 to 0.2% w/w of caprooyl tetrapeptide-3.

* * * * *